United States Patent [19]

Maas, Jr. et al.

[11] 4,119,559

[45] Oct. 10, 1978

[54] UO$_2$F$_2$ INCLUSION COMPOSITIONS

[75] Inventors: Edward T. Maas, Jr., Kendall Park; John M. Longo, New Providence, both of N.J.

[73] Assignee: Exxon Research & Engineering Co., Linden, N.J.

[21] Appl. No.: 752,734

[22] Filed: Dec. 21, 1976

[51] Int. Cl.$^2$ ............................................. C01G 43/00
[52] U.S. Cl. .............................. 252/301.1 R; 423/253; 423/258
[58] Field of Search ................. 252/301.1 R; 423/253, 423/258; 260/429.1

[56] References Cited

PUBLICATIONS

Davidovich, R. L. et al., "Synthesis of Complex Uranyl Fluorides. . . . " Dokl. Akad. Nauk SSSR; 212: No. 5 1114–1117 (Oct. 1973).
Lipovskii, A. A. et al., "Fluoro–Oxalato–Complexes of Uranyl" Russian Journal of Inorganic Chemistry, 14(8), 1969.
Ahuja, I. S. "2,2'-Bipyridin . . . Complexes . . . " Spectrochim. Acta, Part A; 29:No. 10, 1879–1883 (Oct. 1973).
Sanwall, D. N. et al., "Spectral Studies at Some Organic Complexes . . . " Proc. Indian Acad. Sci., Sect. A; 70: 221-33 (Nov. 1969).
Chemical Abstracts 76:92956m 1972.
Chakravorti, M. C. et al., "Fluoro Complexes of Hexavalent Uranium—IV" J. Inorg. Nucl. Chem. 34(9) Sep. 1972 pp. 2867-2874.

*Primary Examiner*—Benjamin R. Padgett
*Assistant Examiner*—Deborah L. Kyle

[57] ABSTRACT

Compositions of matter are described comprising the intercalation of Lewis bases into the layer lattice structure of UO$_2$F$_2$ or by formation of directed chemical bonds between an electron donor atom of the Lewis base and the uranium ions in UO$_2$F$_2$. Thermal treatment of these compositions results in the release of the Lewis base unchanged and the recovery of the uranyl fluoride.

24 Claims, No Drawings

$UO_2F_2$ INCLUSION COMPOSITIONS

BACKGROUND OF THE INVENTION

This invention relates to a composition of matter including $UO_2F_2$ and an organic compound capable of interacting with the $UO_2F_2$.

$UO_2F_2$ is a powder material encountered in the production of $UF_6$, which is subsequently used in isotope enrichment schemes for the production of enriched uranium oxides for use as a fuel in nuclear fission reactors.

$UO_2F_2$ is also the product of hydrolysis of $UF_6$ with water and in certain processing schemes, particularly the fluidized bed hydrolysis of $UF_6$ with dry steam, is isolated and transported as a solid for subsequent reduction to $UO_2$ to be used as a fuel for light water nuclear reactors.

$UO_2F_2$ in powder form is difficult to handle and move in production situations due to the hygroscopic nature of the material and its propensity to cake. The present invention is a composition of matter including $UO_2F_2$. which provides $UO_2F_2$ in a form which eliminates these above stated problems providing a free flowing, non-hygroscopic powdery solid.

Uranyl fluoride prepared at low temperatures is very hygroscopic whereas that prepared at high temperatures exhibits no diliquescence even after extensive contact with air, see J. J. Katz and E. Robinowitch, NNES, VIII-5. The Chemistry of Uranium, Dover Publications, Inc. (1951). This property of uranyl fluoride is exemplified in the $UF_6$ to $UO_2$ conversion process as described by Knudson et al, see I. E. Knudsen, H. E. Hottman, and N. M. Levitz, ANL-6606 (1963). In this described process gaseous $UF_6$ together with dry steam is injected into a fluidized bed of $UO_2F_2$ seed particles to effect hydrolysis of the $UF_6$ to $UO_2F_2$. Even when this process was carried out at a reported 200°-230° C. (which is above the reported decomposition temperature of discrete uranyl fluoride hydrates, a problem was reportedly observed which consisted of the coating of the internal surfaces of the reaction apparatus and subsequent off-gas piping with a layer of $UO_2F_2$ particles. While the rate was not considered excessive, it was estimated that shutdowns for cleaning and deplugging would be necessitated. While it was found that a higher reaction temperature (500° C.) would reduce the caking and plugging problems encountered at lower temperatures, a problem of excessive fines formation resulted. Hence, it can be concluded that for the process to be used effectively a lower temperature must be employed and the product will then exhibit hygroscopic and deliquescent properties.

This is further substantiated in this same referenced report wherein a $UO_2F_2$ product of a low temperature hydrolysis was found to absorb significant amounts of water from the atmosphere during storage in a closed container. Because of the reported hygroscopic and deliquescent tendencies of this low temperature product and the reported difficulty in freeing the $UO_2F_2$ from residual water, it would appear some treatment would be desirable which would permit storage of low temperature preparations of $UO_2F_2$ for long periods of time under ambient conditions without formation of troublesome hydrspecies.

These compositions because of their compositional stoichiometries and stabilities are useful for the storage, transportation and subsequent use of very precisely measured amounts of particular organic Lewis bases which may be required for various chemical reactions involving these Lewis bases.

In addition, these compositions may be included in a process for producing $UO_2F_2$ if the compositions are produced from a reaction of a uranyl salt and a fluoride salt, see discussion below and copending Applns. Ser. No. 752,722 and Ser. No. 752,736 assigned to the same assignee as the present invention, which are incorporated herein by reference.

$UO_2F_2$ exhibits high Lewis acidity and certain of its properties (high metal oxidation state and layered structure) suggest that compositions can be formed by it with molecular Lewis bases.

For example, stable compounds of uranyl fluoride with molecular Lewis bases can be formed by two possible mechanisms. (1) Normal coordination type compounds can be formed in which the Lewis base donates at least a pair of electrons to the central metal ion to form a coordinate covalent bond directly between the electron rich donor atom and the uranium ion. This type of material should exhibit, at equilibrium, an integral ratio of Lewis base to uranium moiety. (2) Because of the structure of $UO_2F_2$, consisting of electrically neutral layers, stable intercalation compounds can be formed by simple insertion of the molecular Lewis base between the layers of the $UO_2F_2$. In this situation, although at equilibrium the Lewis base should assume a definite position in the lattice in relation to the uranium ions, no interaction between the heteroatom(s) of the Lewis base and the uranium ion can be construed because of interatomic distance, geometry and steric interactions to be indicative of formation of discrete, directed chemical bonds. The thermodynamic stability of this type of material arises from van der Waal's interactions and the polarizabilities of the molecular Lewis base and/or the uranyl fluoride lattice. The Lewise base/uranium ratio in these types of compounds has the possibility of assuming either integral or non-integral values.

Lewis base intercalation compounds including metal chalcogenides have been disclosed in the prior art, see German Patent Application 2,061,162, Chalcogenide Inclusion Compounds, F. R. Gamble, et al.

Materials made from Lewis based interacting with $UO_2F_2$ have been disclosed in the prior art. The composition $UO_2F_2 + NH_3$ was disclosed by A. von Unruh, dissertation, University of Rostock (1909) as reported by J. Katz and E. Rabinowitch, The Chemistry of Uranium, Dover Publications, Inc., New York, N.Y.

A composition $[(UO_2F_2)_6.(TBPO)_8]$, where TBPO = $(C_4H_9)_3P = O$, is a polymeric material soluble in benzene was disclosed in the papers by S. M. Sinitsyna and N. M. Sinitsyn, Dokl. Akad, Nauk SSSR 164(2), 851 (1965) and V. M. Vdovenko, A. I. Skoblo, D. N. Suglokov, L. L. Shcerbakova, and V. A. Shcherbakov, Russian Journal of Inorganic Chemistry 12(10) 1513 (1967).

In addition, a hydrate composition, $UO_2F_2.H_2O$, was disclosed in the paper by A. A. Tsvetkov, V. P. Seleznev, B. N. Sudarikov and B. V. Gromov, Russian Journal of Inorganic Chemistry 17(7) 1048 (1972).

None of the compositions referenced above are suitable for the uses discussed above, namely, improvement in the handling characteristics of solid $UO_2F_2$ without sacrificing chemical stability or the ability to provide precise delivery and metering of desired organic Lewis Bases.

SUMMARY OF THE INVENTION

The present invention is, broadly, a composition of matter comprising $UO_2F_2$ and an organic Lewis base capable of interacting with the $UO_2F_2$. The Lewis base may be one of the following: amines, heterocyclic amines, aliphatic heterocyclic amines, aliphatic amides, sulfides, aliphatic heterocyclic sulfides, sulfoxides, aliphatic heterocyclic sulfoxides, sulfones, aliphatic heterocyclic sulfones, alcohols, and mixtures thereof. These bases are further defined below:

The resulting compositions are thermodynamically stable at ambient temperatures and in a form of freely flowing grandular solids. Therefore, the formation of the compositions of the present invention is a process for the retarding the caking properties of $UO_2F_2$.

DESCRIPTION OF THE PREFERRED EMBODIMENT

Compositions of solid materials of the form $UO_2F_2 \cdot L$ may be formed by the interaction of organic Lewis bases; L, with uranyl fluoride $UO_2F_2$. Compositions of this type can be formed because the solid state structure of $UO_2F_2$ is one of electronically neutral two dimensional slabs held to neighboring slabs by rather weak van der Waal attractions.

Therefore, stable intercalation compounds can be formed in which the Lewis base is inserted between these layers. Also, in addition, compounds can be formed by the direct interaction of the electron donor atom of the Lewis base with the uranium ion to form a directed chemical bond.

The type of interaction that prevails and the nature of the resulting composition is an extremely complicated function of the size, shape, functionality, basicity, chemical reactivity and stability of the organic Lewis base and the relationship of all of these factors with the properties of the uranyl fluoride lattice.

When compounds were formed between $UO_2F_2$ and the Lewis bases, the stoichiometry could be characterized by $$\frac{\text{the moles base}}{\text{MOLES } UO_2F_2} = \frac{B}{U} \text{ ratio.}$$

These ratios were typically in the range 0.5–3.0.

Each material isolated exhibited a unique X-ray powder diffraction pattern different from solid $UO_2F_2$ and also different from those of the other compounds indicative of discrete compound formation in each case.

The resulting compounds were isolated in the form of freely flowing granular solids which did not exhibit any hygroscopic properties. Hence, the formation of the compounds of the present invention results in a process for retarding the caking properties of $UO_2F_2$.

The organic Lewis bases that form the compositions of the present invention include generalized classes of nitrogen, sulfur and oxygen containing bases. All of these classes are defined below.

It is to be appreciated that commercial grades of the Lewis bases useful in this invention may contain water. While it is preferable that no water be present, the invention contemplates the use of such bases containing up to about 5% water.

Suitable Lewis bases for the present invention include the following, and mixtures thereof, 1. Amines of generalized formula $$R_1-N(R_3)-R_2$$

where at least one of radicals, $R_1$, $R_2$ and $R_3$ is an aliphatic or an aromatic carbon network with carbon numbers of 1 to 6 with the remaining radicals, if any, being H.

2. Aliphatic heterocyclic amines of generalized formula $$\underset{R_4}{\underset{|}{N}} \diagup (-C(R_{n1})(R_{n2})-)_n \diagdown$$

where $R_4$ is H or an aliphatic radical of carbon number of 1 to 4 and $n$ can assume values of 4 to 6 inclusive and $R_{n1}$ and $R_{n2}$ are each individually H or methyl, each of $R_{n1}$ and $R_{n2}$ being the same or different.

For example, when $n = 4$, then the compound would be

[ring structure with substituents $R_{11}, R_{12}, R_{21}, R_{22}, R_{31}, R_{32}, R_{41}, R_{42}$ and N-$R_4$]

and when $n = 6$, the compound would be

[ring structure with substituents $R_{11}, R_{12}, R_{21}, R_{22}, R_{31}, R_{32}, R_{41}, R_{42}, R_{51}, R_{52}, R_{61}, R_{62}$ and N-$R_4$]

3. Aromatic heterocyclic amines of generalized formula $$\underset{(R_5)_a}{\underset{|}{N}} \diagup (=C(R_{m1})-)_m \diagdown$$

where $m$ is an integer of 4 to 6 inclusive and $a = 1$ when $m = 4$ or 6 and $2 = 0$ when $m = 5$, and $R_5$ is H or aliphatic radical of carbon number 1 to 4 and $R_{m1}$ is H or methyl.

For example when $m = 5$, the compound would be

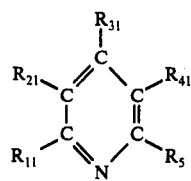

4. Aliphatic amides of formic acid of generalized formula

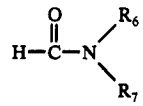

where $R_6$ and $R_7$ are each individually H or an aliphatic radical of carbon number 1 to 3, each of $R_6$ and $R_7$ being the same or different.

An example of this type of compound is

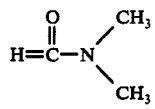

5. Alcohols of generalized formula

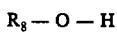

where $R_8$ is an aliphatic radical of carbon number 1 to 4 inclusive.

An example of this type of compound is

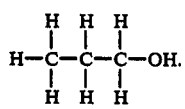

6. Sulfides of generalized formula

where $R_9$ and $R_{10}$ are the same or different aliphatic radicals having a carbon number of 1 to 3.

An example of this type of compound is

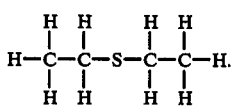

7. Aliphatic heterocyclic sulfides of generalized formula

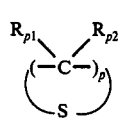

where $p$ is an integer between 4 and 6 inclusive and $R_{p1}$ and $R_{p2}$ are each individually H or methyl, each of $R_{p1}$ and $R_{p2}$ being the same or different.

An example of this type of compound is

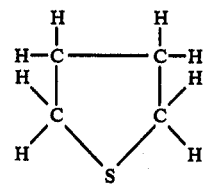

8. Sulfoxides of generalized formula

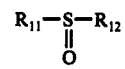

where $R_{11}$ and $R_{12}$ are aliphatic radicals of carbon number 1 to 3.

An example of this type of compound is

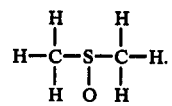

9. Aliphatic heterocyclic sulfoxides of generalized formula

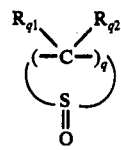

where $q$ is an integer of 4 to 6 inclusive and $R_{q1}$ and $R_{q2}$ are each individually H or methyl, each of $R_{q1}$ and $R_{q2}$ being the same or different.

An example of this type of compound is

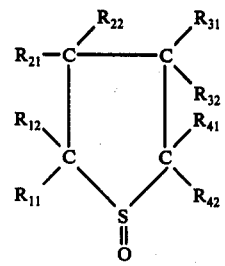

10. Sulfones of generalized formula

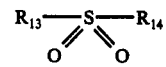

where $R_{13}$ and $R_{14}$ are aliphatic radicals of carbon No. 1 to 3.

An example of this type of compound is

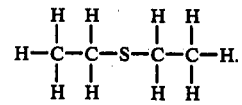

11. Aliphatic heterocyclic sulfones of generalized formula

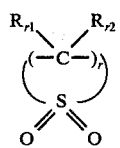

where r is an integer of 4 to 6 inclusive and $R_{r1}$ and $R_{r2}$ are each individually H or methyl, each of $R_{r1}$ and $R_{r2}$ being the same or different.

An example of this type of compound is

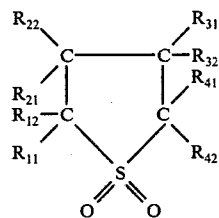

Table I includes specific examples of Lewis bases suitable for the present invention.

TABLE I

BASES THAT REACT WITH $UO_2F_2$ TO FORM $UO_2F_2$

| Base Formula, L | Structure | Stoichiometry (Moles Base/ Mole $UO_2F_2$) |
|---|---|---|
| Pyridine | 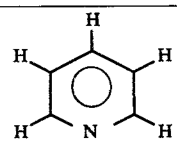 | 0.7 - 2.5 |
| 2-picoline, $C_5H_4(CH_3)N$ | 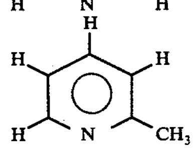 | 0.67 |
| 4-picoline, $C_5H_4(CH_3)N$ | 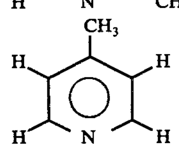 | 1.86 |
| Dimethylsulfoxide $(CH_3)_2SO$ | $H_3C-S-CH_3$ ‖ O | 1.0 |
| N,N-dimethylformamide $HCON(CH_3)_2$ | 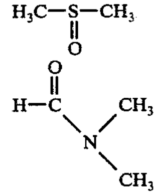 | 1.0 |
| Tetrahydrothiophene $(CH_2)_4S$ | 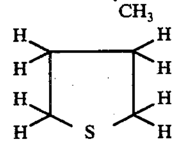 | 0.76 |
| Tetramethylene-sulfoxide $(CH_2)_4SO$ | 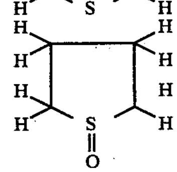 | 1.5 |
| Tetramethylene-sulfone $(CH_2)_4SO_2$ | 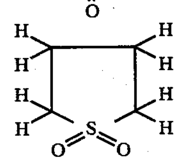 | 1.0 |
| Methyl alcohol | $CH_3OH$ | 1.16 |

TABLE I-continued

BASES THAT REACT WITH $UO_2F_2$ TO FORM $UO_2F_2$

| Base Formula, L | Structure | Stoichiometry (Moles Base/ Mole $UO_2F_2$) |
|---|---|---|
| $CH_3OH$ Ethyl alcohol $C_2H_5OH$ | $CH_3CH_2OH$ | 0.94 |
| n-propyl alcohol $C_3H_7OH$ | $CH_3CH_2CH_2OH$ | 0.95 |
| Aniline | 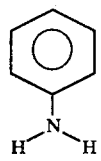 | 0.8 |

TABLE II

TEMPERATURES FOR THE RECOVERY OF $UO_2F_2$

| Base (B/$UO_2F_2$) | T (Peak) |
|---|---|
| py (0.7) | 210° C |
| py (1.65) | 110° C |
| 4-picoline (1.86) | 130° C |
| 2-picoline (0.67) | 225° C |
| DMF (1.0) | 220° C |
| DMSO (1.0) | 340° C |
| THF (0.76) | 300° C |
| THTO (1.5) | 90/300° C |
| THTO$_2$ (1.0) | 130° C |
| MeOH (1.16) | 135° C |
| EtOH (0.94) | 90° C |
| n-prOH (0.95) | 110° C |
| Aniline (0.8) | 250° C |

Compositions of the above-described type were prepared by treating solid uranyl fluoride with the organic Lewis base. The base may be either liquid or gaseous and may in each case be diluted with an inert material. For example, the liquid organic Lewis base may be diluted with benzene or acetone before it is contacted with the solid uranyl fluoride. Likewise the organic Lewis base in gaseous form may be diluted with nitrogen gas and then passed over the solid uranyl fluoride to effect reaction. The temperature of the reaction may be varied with the lower limit being, in each specific case, the solidification temperature of the particular organic Lewis base and the upper limit in each case being the temperature at which decomposition of the product compound is initiated.

The time for an equilibrium content of organic Lewis base to be included by the $UO_2F_2$ varies depending on the chemical activity of the base in question. That is to say, an organic base in concentrated liquid form has a higher chemical activity towards reaching an equilibrium concentration in the resulting compound than that of a gas stream consisting of, for example, only 0.5-1.0% or less of the same base in gaseous form. In general with neat liquid bases, 24-36 hours reaction times are necessary for complete reaction to occur at ambient temperatures (20° C). When the organic is presented in vapor form to the uranyl fluoride, longer reaction times on the order of 3-7 days are necessary depending upon the vapor pressure of the organic base and the temperature of the reaction.

An increase in the temperature at which the reaction is carried out will also cause an increase in the rate of the reaction. For example, contacting $UO_2F_2$ with refluxing pyridine will shorten the reaction time to about 1-2 hours.

In order for the reaction to be accomplished easily, a sufficient quantity of base must be present to insure adequate liquid (or gas)/solid contact. Therefore, when a liquid base is involved, a sufficient quantity of liquid to completely cover and wet the sample must be employed. For example, a 1 cc sample of $UO_2F_2$ having a theoretical density of 6.438g/cc would contain 0.0209 moles. In order that at least stoichiometric amount of base contact this amount of $UO_2F_2$ (equilibrium values of Base/$UO_2F_2$ ranging from 0.5 to 3.0) 0.0105 to 0.0627 moles of Lewis base should be employed. Assuming a nominal density for organic liquids of ca. 1.0 g/cc, and a molecular weight of 80 g/mole, 0.85 cc to 5.0 cc of the bases should be employed. More than these quantities of organic Lewis bases could be employed without adverse interferences. Preferably, at least 2 cc of the liquid organic Lewis base should be used per 1 cc of the solid $UO_2F_2$.

$UO_2F_2$ is soluble in low molecular weight alcohols and in these cases the solid complex was isolated by evaporation of the excess organic base. When water (or water vapor) was present in appreciable amounts together with the organic bases, mixed complexes containing both water and the organic base were formed with $UO_2F_2$. This was found to be the case especially in the pyridine/$UO_2F_2$ system.

Also, the ability of $UO_2F_2$ to react with organic Lewis bases diluted by inert substances allows one to use $UO_2F_2$ as a separating agent to remove certain organic bases from the bulk solution. That is, the $UO_2F_2$ acts as a trap on the molecular level to selectively remove certain basic components from mixtures of either liquids and/or gases. Both the trapped base and the $UO_2F_2$ could then be recovered by thermal treatment of the thus formed compound as described previously.

Compounds of the present invention may also be prepared by reacting a soluble uranyl salt (uranyl = $UO_2^{2+}$) with a soluble fluoride salt in a solvent which includes the above described Lewis bases. Preferred uranyl salts are uranyl acetate and uranyl nitrate. A preferred fluoride salt is ammonium fluoride ($NH_4F$).

The uranyl salt is added to the solvent in an amount to produce a solution with the concentration of uranium within the range 0.005 moles U/l and 0.50 moles U/liter.

A separate solution of the fluoride salt is made up in the same solvent within a concentration range of 0.01 moles F/liter and 1.0 moles F/liter. The two solutions are then mixed to effect reaction.

Preferably the uranium concentration is in the range 0.02 moles U/liter and 0.42 moles U/liter. The preferable fluoride concentrations are in the range 0.04 moles F/liter and 0.84 moles F/liter. The fluoride concentration must be maintained at a level as to produce a F/U ratio in the final solution of about 2.00 in order to affect quantitative precipitation of the uranium and in order to protect the integrity and identity of the product.

Water may be contained in the solution up to the equivalent of 10 moles $H_2O$/mole U and preferably a maximum of 6 moles $H_2O$/mole U. This water may be present in the solvent or may be added because of the hydrated nature of many soluble uranyl salts and/or fluoride salts.

The temperature of the reaction solution is maintained between about 20° C and about 125° C and preferably between 80° C. and 110° C. for a period of time between 0.5 and 5.0 hours.

The uranyl salt and the fluoride salt react to form the compositions of matter in the form of a crystalline solid. The crystalline solid is easily separated from the reaction solution by common well-known techniques such as filtration or centrifugation. After washing with a small amount of pure solvent to remove any soluble counter ions present, the product can then be air dried or vacuum dried.

What is claimed is:

1. A composition of matter comprising an inclusion compound formed by reacting $UO_2F_2$ and an organic Lewis base, the molar ratio of Lewis base to $UO_2F_2$ in said composition varying in the range from 0.5 to 3.0, said Lewis base selected from the group consisting of
amines of generalized formula

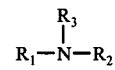

where at least one of radicals $R_1$, $R_2$ and $R_3$ is an aliphatic or an aromatic carbon network with carbon numbers of 1 to 6 with the remaining radicals, if any, being H,
aliphatic heterocyclic amines of generalized formula

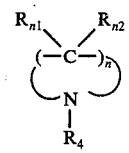

where $R_4$ is H or an aliphatic radical of cabon number of 1 to 4 and $n$ can assume values of 4 to 6 inclusive and $R_{n1}$ and $R_{n2}$ are each individually H or methyl, each of $R_{n1}$ and $R_{n2}$ being the same or different,
aromatic heterocyclic amines of generalized formula

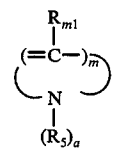

where $m$ is an integer of 4 to 6 inclusive and $a = 1$ when $m = 4$ or 6 and $a = 0$ when $m = 5$, and $R_5$ is H or aliphatic radical of carbon number 1 to 4 and $R_{m1}$ is H or methyl,
aliphatic amides of formic acid of generalized formula

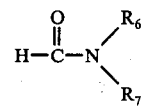

where $R_6$ and $R_7$ are each individually H or an aliphatic radical of carbon number 1 to 3, each of $R_6$ and $R_7$ being the same or different,
alcohols of generalized formula

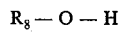

where $R_8$ is an aliphatic radical of carbon number 1 to 4,
sulfides of generalized formula

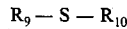

where $R_9$ and $R_{10}$ are the same or different aliphatic radicals having a carbon number of 1 to 3, aliphatic heterocyclic sulfides of generalized formula

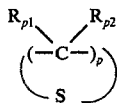

where $p$ is an integer between 4 and 6 inclusive and $R_{p1}$ and $R_{p2}$ are each individually H or methyl, each of $R_{p1}$ and $R_{p2}$ being the same or different, aliphatic heterocyclic sulfoxides of generalized formula

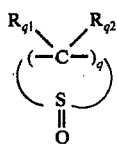

where $q$ is an integer of 4 to 6 inclusive and $R_{q1}$ and $R_{q2}$ are each individually H or methyl, each of $R_{q1}$ and $R_{q2}$ being the same or different, sulfones of generalized formula

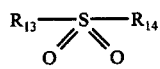

where $R_{13}$ and $R_{14}$ are aliphatic radicals of carbon number 1 to 3, aliphatic heterocyclic sulfones of generalized formula

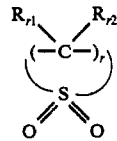

where $r$ is an integer of 4 to 6 inclusive and $R_{r1}$ and $R_{r2}$ are each individually H or methyl, each of $R_{r1}$ and $R_{r2}$ being the same or different, and mixtures thereof.

2. The composition of claim 1 in which said Lewis base is an amine.

3. The composition of claim 1 in which said Lewis base is an aliphatic heterocyclic amine.

4. The composition of claim 1 in which said Lewis base is an aromatic heterocyclic amine.

5. The composition of claim 1 in which said Lewis base is an aliphatic amide.

6. The composition of claim 1 in which said Lewis base is an alcohol.

7. The composition of claim 1 in which said Lewis base is a sulfide.

8. The composition of claim 1 in which said Lewis base is an aliphatic heterocyclic sulfide.

9. The composition of claim 1 in which said Lewis base is an aliphatic heterocyclic sulfoxide.

10. The composition of claim 1 in which said Lewis base is a sulfone.

11. The composition of claim 1 in which said Lewis base is an aliphatic heterocyclic sulfone.

12. The composition of matter of claim 1 in which the Lewis base is selected from the group consisting of pyridine, 2-picoline, 4-picoline, N,N-dimethylformamide, tetrahydrothiophene, tetramethylenesulfoxide, tetramethylenesulfone, methyl alcohol, ethyl alcohol, n-propyl alcohol, aniline and mixtures thereof.

13. The composition of matter of claim 12 in which said Lewis base is pyridine.

14. The composition of matter of claim 12 in which said Lewis base is 2-picoline.

15. The composition of matter of claim 12 in which said Lewis base is 4-picoline.

16. The composition of matter of claim 12 in which said Lewis base is N,N-dimethylformamide.

17. The composition of matter of claim 12 in which said Lewis base is tetrahydrothiophene.

18. The composition of matter of claim 12 in which said Lewis base is tetramethylenesulfoxide.

19. The composition of matter of claim 12 in which said Lewis base is tetramethylenesulfone.

20. The composition of matter of claim 12 in which said Lewis base is methyl alcohol.

21. The composition of matter of claim 12 in which said Lewis base is ethyl alcohol.

22. The composition of matter of claim 12 in which said Lewis base is n-propyl alcohol.

23. The composition of matter of claim 12 in which said Lewis base is aniline.

24. A process for retarding the caking properties of $UO_2F_2$ comprising (a) contacting solid uranyl fluoride with a Lewis base until a compound is formed, the molar ratio of Lewis base to uranyl fluoride in said compound varying in the range from 0.5 to 3.0, said Lewis base selected from the group consisting of amines of generalized formula

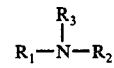

where at least one of radicals $R_1$, $R_2$ and $R_3$ is an aliphatic or an aromatic carbon network with carbon numbers of 1 to 6 with the remaining radicals, if any being H, aliphatic heterocyclic amines of generalized formula

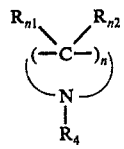

where $R_4$ is H or an aliphatic radical of carbon number of 1 to 4 and $n$ can assume values of 4 to 6 inclusive and $R_{n1}$ and $R_{n2}$ are each individually H or methyl, each of $R_{n1}$ and $R_{n2}$ being the same or different, aromatic heterocyclic amines of generalized formula

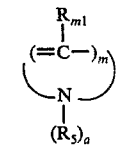

where $m$ is an integer of 4 to 6 inclusive and $a = 1$ when $m = 4$ or 6 and $a = 0$ when $m = 5$, and $R_5$ is H or aliphatic radical of carbon number 1 to 4 and $R_{m1}$ is H or methyl, aliphatic amides of formic acid of generalized formula

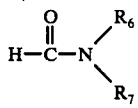

where $R_6$ and $R_7$ are each individually H or an aliphatic radical of carbon number 1 to 3, each $R_6$ and $R_7$ being the same or different, alcohols of generalized formula

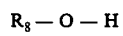

where $R_8$ is an aliphatic radical of carbon number 1 to 4, sulfides of generalized formula

where $R_9$ and $R_{10}$ are the same or different aliphatic radicals having a carbon number of 1 to 3, aliphatic heterocyclic sulfides of generalized formula

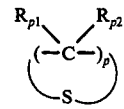

where $p$ is an integer between 4 and 6 inclusive and $R_{p1}$ and $R_{p2}$ are each individually H or methyl, each of $R_{p1}$ and $R_{p2}$ being the same or different, aliphatic heterocyclic sulfoxides of generalized formula

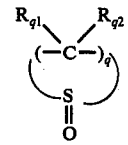

where $q$ is an integer of 4 to 6 inclusive and $R_{q1}$ and $R_{q2}$ are each individually H or methyl, each or $R_{q1}$ and $R_{q2}$ being the same or different, sulfones of generalized formula

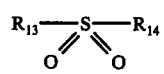

where $R_{13}$ and $R_{14}$ are aliphatic radicals of carbon number 1 to 3, and aliphatic heterocyclic sulfones of generalized formula

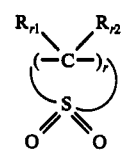

where $r$ is an integer of 4 to 6 inclusive and $R_{r1}$ and $R_{r2}$ are each individually H or methyl, each of $R_{r1}$ and $R_{r2}$ being the same or different, and mixtures thereof;

(b) recovering said $UO_2F_2$ containing compound.

* * * * *